United States Patent [19]
Wang et al.

[11] Patent Number: 5,219,727
[45] Date of Patent: Jun. 15, 1993

[54] QUANTITATION OF NUCLEIC ACIDS USING THE POLYMERASE CHAIN REACTION

[75] Inventors: Alice M. Wang, Walnut Creek; Michael V. Doyle, Oakland, both of Calif.; David F. Mark, Plainsboro, N.J.

[73] Assignee: Hoffmann-LaRoche Inc., Nutley, N.J.

[21] Appl. No.: 413,623

[22] Filed: Sep. 28, 1989

Related U.S. Application Data

[63] Continuation-in-part of Ser. No. 396,986, Aug. 21, 1989, abandoned.

[51] Int. Cl.$^5$ .................... C12Q 1/68; C12P 19/34; C12N 15/00; C07H 21/04
[52] U.S. Cl. .................................. 435/6; 435/91; 536/24.33; 935/77; 935/78
[58] Field of Search ............... 435/6, 810, 91; 536/27; 935/77, 78; 436/501, 808

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,889,818 | 12/1989 | Gelfand et al. | 435/194 |

FOREIGN PATENT DOCUMENTS 8810315 6/1988 PCT Int'l Appl.

OTHER PUBLICATIONS

Kwok et al., Nature, vol. 339, May 18, 1989, pp. 237-238.
Chelly et al., Nature, vol. 333, Jun. 30, 1988, pp. 858-860.
Chelly et al., 1990, Eur. J. Biochem. 187(3)691-698 (Abstract submitted).
Becker-Andre and Hahlbrock, 1989, Nuc. Acids Res. 17(22):9437-9446.
Horn et al, 1988, Proc. Acad. Sci. USA 85:6012-6016.
Kawasaki et al., 1988, Prod. Natl. Acad. Sci. USA 85:5698-5702.
Myerowitz, 1988 Proc. Natl. Acad. Sci. USA 85:3955-3959.
Neri et al., 1988 Proc. Natl. Acad. Sci. USA 85:9268-9272.
Todd et al., 1987, Nature 329:599-604.
Wu et al., 1989, Proc. Natl. Acad. Sci. USA 86:2757-2760.
Chelly et al., Jun. 1988, Nature 333:858-860.
Gilliland et al., Apr. 3-24, 1989, J. Cellular Biochemistry, UCLA Symposia on Molecular and Cellular Biology, Abstract WH001.
Kashani-Sabet et al., Oct. 1988, Cancer Research 48:5775-5778.
Rappolee et al., 1988, Science 241:708-712.
Smith et al., 1989, J. Immunological Methods 118:265-272.
Chomczynski and Sacchi, 1987, Analytical Biochemistry 162:156-159.
Gerard, 1987, Focus (Bethesda Res. Labs) 9:5.
Higuchi et al., 1988, Nucl. Acids Res. 16(15):7351-7367.
Ho et al., 1989, Gene, 77:51-59.
Okayama and Berg. 1983, Molecular Cellular Biology 3(2):280-289.

(List continued on next page.)

Primary Examiner—Margaret Moskowitz
Assistant Examiner—Mindy B. Fleisher
Attorney, Agent, or Firm—George M. Gould; Dennis P. Tramaloni; Stacey R. Sias

[57] ABSTRACT

The present invention provides a method for determining the amount of a target acid segment in a sample by polymerase chain reaction. The method involves the simultaneous amplification of the target nucleic acid segment and an internal standard nucleic acid segment. The amount of amplified DNA from each segment is determined and compared to standard curves to determine the amount of the target nucleic acid segment present in the sample prior to amplification. The method is especially preferred for determining the quantity of a specific mRNA species in a biological sample. Additionally, an internal standard is provided useful for quantitation of multiple mRNA species.

10 Claims, 4 Drawing Sheets

U.S. PATENT DOCUMENTS

Rappolee et al., 1989, *J. Cellular Biochemistry* 39:1–11.
Syvanen et al., 1986, *Nuc. Acids Res.* 14(12):5037–5048.
Syvanen et al., 1988, *Nuc. Acids. Res.* 16(23):11327–11338.
Gilliland et al., "Competitive PCR for Quantitation of mRNA".
Wang et al., 1989, *Proc Natl. Acad. Sci. USA* 86:9717–9721.
Betsholtz et al., 1986, *Nature* 320:695–699.
Claesson-Welsch et al., 1988, *Molecular Cellular Biology* 8(8):3476–3486.
Collins et al., 1985, *Nature* 316:748–750.
Fujita et al., 1983, *Proc. Natl. Acad. Sci. USA 80:7437–7441.*
Kawasaki et al., 1985, *Science* 230:291–294.
Luskey and Stevens, 1985, *J. Biological Chemistry* 260(18):10,271–10,277.
March et al., 1985, *Nature 315:641–647.*
Nedwin et al., 1985, *Nuc. Acids Res.* 13:6361–6373.
Paik et al., 1985, *Proc. Natl. Acad. Sci. USA* 82:3445–3449.
Wion et al., 1987, *Science* 235:1638–1641.
Yamamoto et al., 1984, *Cell* 39:27≧38.
Abbott et al., 1988, *J. Infectious Diseases* 158(6):1158–1169.
Barrett and Benditt, 1987, *Proc. Natl. Acad. Sci. USA* 84:1099–1103.
Barrett and Benditt, 1988, *Proc. Natl. Acad. Sci. USA* 85:2810–2814.
Horton et al., 1989, *Gene* 77:61–68.
Larzul et al., 1988, *J. Virological Methods* 20:227–237.

←420bp
←308bp

QUANTITATION OF NUCLEIC ACIDS USING THE POLYMERASE CHAIN REACTION

CROSS REFERENCE TO RELATED APPLICATION

This application is a continuation-in-part of copending U.S. Ser. No. 396,986, filed Aug. 21, 1989 now abandoned.

BACKGROUND OF THE INVENTION

1. Field of the Invention

The present invention relates to the quantitative determination of a particular nucleic acid segment in a sample. The invention is particularly useful for determining the quantity of specific mRNA molecules in a biological sample. The method is therefore especially applicable in the field of medical diagnostics but can also be applied in the fields of genetics, molecular biology, and biochemistry.

2. Description of Related Disclosures

U.S. Pat. Nos. 4,683,195 and 4,683,202 disclose methods for carrying out the polymerase chain reaction (PCR), a nucleic acid amplification method, and for using PCR in the detection of specific nucleotide sequences. European Patent Office Publication (EPO) No. 258,017 describes Taq polymerase, a preferred DNA polymerase for use in PCR. These publications are incorporated by reference herein.

PCR methods have widespread applications in genetic disease diagnosis (see Wu et al., 1989, *Proc. Natl. Acad. Sci. USA* 86:2757–2760 and Myerswitz, 1988, *Proc. Natl. Acad. Sci. USA* 85:3955–3959), as well as disease susceptibility and cancer diagnosis (see Horn et al., 1988, *Proc. Natl. Acad. Sci. USA* 85:6012–6016; Todd et al., 1987, *Nature* 329:599–604; Kawasaki, 1988, *Proc. Natl. Acad. Sci. USA* 85:5698–5702; and Neri et al., 1988, *Proc. Natl. Acad. Sci. USA* 85:9268–9272). However, these uses have provided only qualitative results by, for example, detecting unique mRNA transcripts from abnormal cells in a background of normal cells.

An attempt to use PCR for quantitative studies of mRNA level for thymidylate synthase in tumors has been published (see Kashani-Sabet, 1988, *Cancer Res.* 48:5775–5778). However, this study provides only relative comparisons of amounts of mRNA in biological samples. It has been much more difficult to quantitate the absolute amount of specific mRNA without an internal standard of known concentration. Other methods have been described for quantitating nucleic acid species by using PCR to co-amplify a second, unrelated, template cDNA (see Chelly et al., 1988, *Nature* 333:858–860 and Rappolee et al., 1988, *Science* 241:708–712). The use of an unrelated cDNA standard also necessitates the use of a second set of oligonucleotide primers, unrelated to the specific target mRNA.

Because amplification is an exponential process, small differences in any of the variables which control the reaction rate, including the length and nucleotide sequence of the primer pairs, can lead to dramatic differences in the yield of PCR product. Analyses which use two sets of unrelated primers, therefore, can only provide a relative comparison of two independent amplification reactions rather than an absolute measure of mRNA concentration.

Gilliland et al. (*J. Cellular Biochemistry*, UCLA Symposia on Molecular and Cellular Biology, Apr. 3–21, 1989, Abstract WH001) describe alternative approaches to mRNA quantitation to avoid some of the problems associated with unrelated templates as amplification standards. However, the Gilliland et al. suggestions have other inherent limitations. One approach requires mapping of genomic introns and exons for the gene corresponding to a specific target mRNA. Gilliland et al. also proposes an alternative approach using site directed mutagenesis to construct an internal standard, which causes the formation of heteroduplexes following amplification. These heteroduplexes result in an over estimation of the amount of target sequence present in the original sample. Smith et al. (Smith et al., 1989, *J. Immunol. Meth.* 118:265–272) have used an RNA dot blot assay to asses quantitatively the expression level of the two IL-1 mRNAs in human macrophages. Smith et al. reported that the level of sensitivity for IL-1α mRNA was approximately $10^7$ molecules by his method, and IL-1α mRNA was undetected in uninduced macrophages. The present invention provides a quantitation method which can readily measure $10^4$ molecules and readily detects IL-1α mRNA in uninduced as well as induced macrophages in a sample assay. This 1000 fold increase in sensitivity represents an important advance in quantitative analysis for clinical and research purposes.

There remains a need for a method to quantitate directly, accurately, and reproducibly the amount of a specific nucleic acid segment in a sample. The availability of quantitative PCR will provide valuable information in a number of research areas. More particularly, the invention provides critical information in disease diagnosis and cancer therapy. For example, a reliable, sensitive, quantitative analysis can be critical in determining the extent of induction of mRNA synthesis in response to exogenous stimuli. The present invention overcomes the numerous limitations inherent in the attempts of others in this field, and thus provides means for accurately quantifying the amount of a nucleic acid segment in a biological sample.

SUMMARY OF THE INVENTION

The present invention provides a method for quantifying a target nucleic acid segment in a sample, which method comprises the steps of:

(a) adding to said sample an amount of standard nucleic acid segment;

(b) treating said sample under conditions suitable for carrying out a polymerase chain reaction, wherein said nucleic acids are rendered single-stranded and exposed to an agent for polymerization, deoxynucleoside 5' triphosphates, and a pair of oligonucleotide primers, wherein said pair of primers is specific for both the target and standard nucleic acid segments, such that an extension product of each primer of said pair can be synthesized using separate strands of the target and standard segments as a template for synthesis, such that the extension product of one primer, when it is separated from the remplate strand, can serve as a template for the synthesis of the extension product of the other primer of said pair;

(c) separating the primer extension product from the templates on which they were synthesized to form single-stranded molecules;

(d) repeating steps (b) and (c) on the single stranded molecules produced in step (c) at least once, whereby each repeat of steps (b) and (c) is one amplification cycle;

(e) measuring the amounts of the amplified target and standard segments produced in step (d); and (f) calculating from the amplified target and standard segments produced in step (d) the amount of said target nucleic acid segment present in the sample before amplification.

The present invention also provides a plasmid useful for providing an internal standard for quantitation of target nucleic acid segments, said plasmid comprising a DNA sequence, said DNA sequence further comprising sequences which are identical to DNA sequences contained within said target nucleic acid segments.

The present invention also provides kits for the quantitation of specific nucleic acid segments in a biological sample.

DESCRIPTION OF THE FIGURES

FIG. 2A depicts an ethidium bromide stained acrylamide gel wherein the amplified standard and target DNA segments are visible.

FIG. 2B plots the amounts of standard and target IL-1α PCR product DNA produced against template concentrations.

FIG. 2C shows a plot of the amounts of standard and template IL-1α PCR product DNA produced versus the number of amplification cycles.

DETAILED DESCRIPTION OF THE INVENTION

Figure 1:
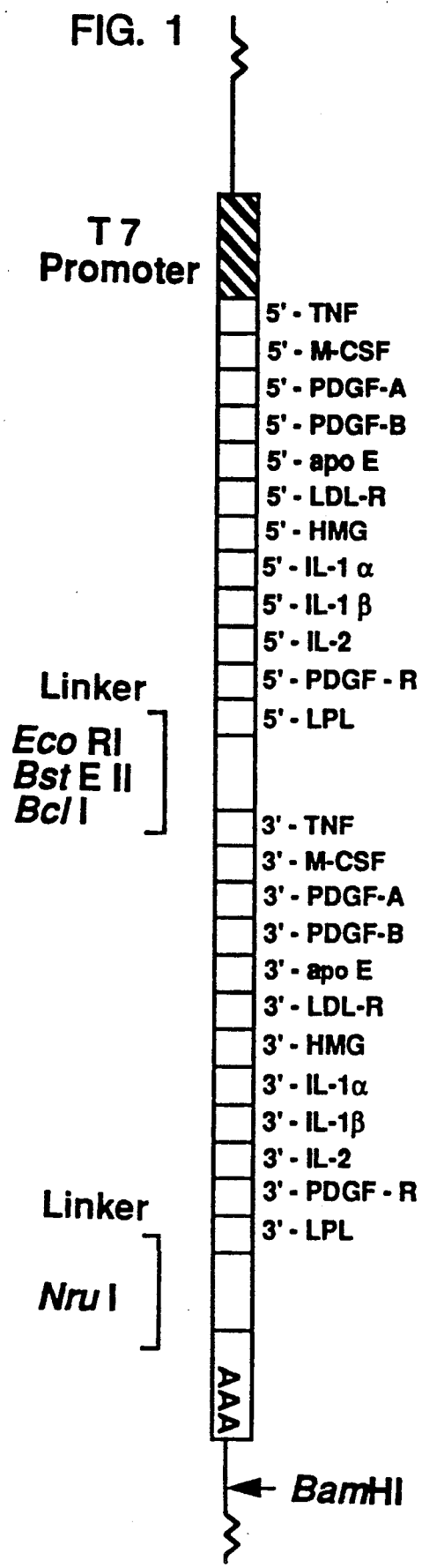
FIG. 1 shows the positions of the 5' primers and 3' primers of Table I as they are arranged in plasmids AW108 and AW109. Other features are shown as they relate to the present invention.

The present invention provides a method for determining the absolute amount of a nucleic acid segment in a sample. The method involves amplification, by a polymerase chain reaction, of two different segments of nucleic acid combined in one reaction mix. The two segments include a target segment and an internal standard segment. The internal standard is amplified using the same oligonucleotide primer pair as the target nucleic acid; however, the two nucleic acid segments yield amplified products which are distinguishable by size.

The standard segment is present in a known amount. Following amplification, the amount of each of the two polymerase chain reaction products is measured, and the amount of the target segment present in the original sample is quantitated by extrapolating against a standard curve. In addition, the internal standard described herein contains primer sequences for multiple genes, so that the same standard can be used to quantitate a number of different nucleic acid segments of interest.

The present invention has particular utility in providing a rapid, sensitive, and reliable method for accurately determining the quantity of low abundance, specific mRNAs present in a sample containing less than 0.1 ng of total RNA. The method provides an approach powerful enough to enable a measurement of heterogeneity of expression levels of specific mRNAs within particular subpopulations even at the single cell level.

By co-amplification of the target nucleic acid and the internal standard nucleic acid, variable effects are internally controlled and affect the yield of PCR product equally for target and standard nucleic acids. Numerous variables influence the rate of the PCR reaction. Such variables may include the concentrations of polymerase, dNTPs, $MgCl_2$, nucleic acid templates, and primers, as well as the rate of "primer-dimer" formation and tube-to-tube variations.

The amount of the target nucleic acid segment present in the sample prior to amplification is determined using a standard curve. The standard curve is generated by plotting the amount of the standard segment produced in a polymerase chain reaction against varying, but known, amounts of the RNA present before amplification. For accuracy, the amount of standard segment present before amplification is varied by serial dilution of the co-amplification reaction mix. The amount of target segment produced in the polymerase chain reaction is then compared to the standard curve to determine the amount of target segment present in the sample prior to amplification. Alternatively, the standard curve may be generated by plotting the amount of standard and target segments produced against the number of amplification cycles. To ensure accuracy, it is preferred that the number of amplification cycles is varied by removing aliquots from one co-amplification reaction mixture after different numbers of amplification cycles have been completed.

The method of the invention is far superior to determinations of the amount of a nucleic acid segment in a sample as a relative, rather than absolute, amount. Further, the method is far more accurate than when an absolute amount is derived by employing a second set of oligonucleotide primers to amplify the standard, wherein that set of primers is different from the set used to amplify the target segment.

The method of the present invention is useful for quantifying a target RNA or DNA molecule. For determining an amount of DNA present in a sample, amplification methods described herein can be applied directly. As the examples disclosed below will demonstrate, the present invention is also useful in determining the amount of a specific mRNA in a sample of total RNA. The internal standard nucleic acid segment is provided on a DNA plasmid. The presence of an appropriately placed T7 polymerase promoter or another suitable promoter, such as the SP6 promoter, allows the plasmid to be used as a template for cRNA synthesis. As defined herein for the purpose of the present invention, the term "cRNA" refers to a ribonucleic acid synthesized from a DNA template by an RNA polymerase. Further, the plasmid may contain a polyadenylation sequence at the 3' end to facilitate purification and subsequently quantitation of the in vitro synthesized cRNA. As described in the preferred embodiments, the DNA template is either plasmid AW108 or AW109, and the RNA polymerase is T7 polymerase. In one embodiment AW108 cRNA is synthesized as a sense strand from pAW108 by T7 polymerase. The structure of pAW108 is shown in FIG. 1. The primer array as shown in FIG. 1 is identical for both pAW108 and pAW109. The cRNA molecule then serves as the internal standard template for reverse transcription by the DNA polymerase, reverse transcriptase. Reverse transcriptase generates a cDNA transcript from an RNA template. The preferred embodiment of the invention, the internal standard cRNA, is synthesized as a sense strand. Following reverse transcription of the target mRNA and the standard cRNA, PCR is then performed.

As will be obvious to those skilled in the art, numerous methods are known for constructing plasmids useful in the method of the present invention. Higuchi, 1988, *Nucleic Acids Research* 16:7351–7367 and Ho, 1989, *Gene* 77:51–59 describe two methods for engineering novel plasmids which incorporate desired synthetic DNA sequences. Alternatively, synthetic DNA segments can be inserted via restriction enzyme digestion and ligation with an appropriately treated parent plasmid or phage vector. The internal standard of the preferred embodiment, pAW108, contains multiple primer sets which allow a single cRNA standard to be used to quantitate a number of different mRNAs. The presence of unique restriction enzyme sites in the pAW108 plasmid provides the flexibility to add new primer sets to the plasmid. The unique BamHI site is used to linearize the plasmid to produce a linear template for reverse transcription. A deposit of *E. coli* containing plasmid AW108 has been deposited with the American Type Culture Collection (ATCC) at 12301 Parklawn Drive, Rockville, Md. according to the terms of the Budapest Treaty. A deposit of *E. coli* containing plasmid AW109 has also been deposited with the American Type Culture Collection (ATCC) at 12301 Parklawn Drive, Rockville, Md. according to the terms of the Budapest Treaty.

Plasmid AW108 is derived from pcDV1 and pL1 which are disclosed in Okayama and Berg, 1983, *Mol. Cell Biol.* 3:280–289. The SV40 promotor region from pLI was inserted into pcDV1 as directed in the referenced article. The T7 promoter, synthetic oligonucleotide sequences, and a polyadenylation region from the IL-1α gene were then inserted to provide the AW108 plasmid as an internal standard for the quantitation of twelve specific mRNAs. The plasmid was transformed into *E. coli* and grown in Luria Broth with ampicillin at 50 μl/ml added.

Plasmid AW108 was subsequently used as the starting material to construct pAW109. A culture of *E. coli* containing pAW108 was grown, and plasmid DNA was purified by standard means. The plasmid was digested with BamHI and BglII restriction endonucleases, and the 1 kb fragment was purified. This fragment contained the 5' and 3' primer arrays shown in FIG. 1 as well as the polyadenylation sequence. Plasmid pSP72 (Promega Biotec, Madison, Wis. contains a T7 promoter adjacent to a polylinker to facilitate cloning. The plasmid also contains the ampicillin resistance gene.

The BglII-BamHI fragment from pAW108 was ligated into BglII and BamHI cleaved pSP72. Both of these are unique restriction sites within the polylinker region. The ligation mixture was used to transform *E. coli* DH5α, and resultant ampicillin resistant colonies were selected. The plasmid was assayed for the correct orientation of the BglII-BamHI insert. The resulting plasmid, pAW109, is suitable as an internal standard for mRNA quantitation.

As will be obvious to those skilled in the art, numerous other plasmids are available for insertion of desired DNA sequence to provide an internal standard useful in the present invention. Generally, the methods for transformation of such plasmids into a suitable host strain, propagation of the transformed host, and preparation of plasmid DNA as required for practice of the invention can be found in Maniatis et al., *Molecular Cloning—A Laboratory Manual*, Cold Spring Harbor Laboratory, Cold Spring Harbor, N.Y., 1985.

As used herein, the term "5' primer" refers to an oligonucleotide comprising a sequence identical to the sequence contained within the sense strand of a target nucleotide segment. As used herein the term "3' primer" refers to an oligonucleotide comprising a sequence complementary to a sequence contained within the sense strand of the same target nucleotide segment. Thus, a 3' primer useful in the method of the present invention will hybridize to an mRNA, cRNA, or DNA template. It is further descriptive of the 3' and 5' primers that for both the internal standard cRNA and the target mRNA segment, the region of 3' primer hybridization is located 3' to the region of 5' primer hybridization.

The 3' and 5' primers function in the method of the present invention as follows: the 3' primer primes DNA synthesis in a PCR reaction to produce an antisense DNA strand, which provides a template for second strand DNA synthesis when the 5' primer is included in the PCR reaction. Such a 5' and 3' primer are referred to herein as a "primer pair."

In the preferred embodiment, most members of a primer pair are designed to span two exon-intron junctions within the gene encoding each target mRNA. In this way the primers will only hybridize effectively to the desired target mRNA. Thus, small amounts of contaminating genomic DNA in a biological sample will not effect accurate quantitation of the target mRNA.

Thus, a primer pair will function in a PCR reaction to amplify a segment of nucleic acid having a primer sequence identical to a DNA segment contained within the standard nucleic acid, i.e., as illustrated here, plasmids AW108 and AW109. As described herein, both plasmids contain a DNA sequence which comprises the DNA sequence of twelve primer pairs arranged as follows: DNA identical in sequence to the 5' primers of twelve target mRNAs is followed by the complementary DNA sequence of the 3' primers for the same twelve target mRNAs (FIG. 1). The primer pair DNA sequence within pAW108 and pAW109 corresponds to mRNAs encoding tumor necrosis factor (TNF), macrophage-colony stimulating factor (M-CSF), platelet-derived growth factor A (PDGF-A), platelet-derived growth factor B (PDGF-B), low density lipoprotein receptor (LDL-R), 3-hydroxy-3-methylglutaryl coenzyme A reductase (HMG), interleukin-1α (IL-1α), interleukin-1β (IL-1β), interleukin-2 (IL-2), type beta platelet-derived growth factor receptor (PDGF-βR), and lipoprotein lipase (LPL). The primer pairs useful for amplifying the internal standard provided by AW108 or AW109 cRNA in the practice of the method of the invention are depicted in Table I.

TABLE I

Oligonucleotides of 12 Target Genes' 5' Primers and 3' Primers

| mRNA Species | 5' Primers | 3' Primers | Size of PCR Product (bp) mRNA | cRNA |
|---|---|---|---|---|
| TNF | 5'-CAGAGGGAAGACTTCCCCAG-3' | 5'-CCTTGGTCTGGTAGGAGACG-3' | 325 | 301 |
| M-CSF | 5'-GAACAGTTGAAAGATCCAGTG-3' | 5'-TCGGACGCAGGCCTTGTCATG-3' | 171 | 302 |
| PDGF-A | 5'-CCTGCCCATTCGGAGGAAGAG-3' | 5'-TTGGCCACCTTGACGCTGCG-3' | 225 | 301 |
| PDGF-B | 5'-GAAGGAGCCTGGGTTCCCTG-3' | 5'-TTTCTCACCTGGACAGGTGG-3' | 217 | 300 |
| apo-E | 5'-TTCCTGGCAGGATGCCAGGC-3' | 5'-GGTCAGTTGTTCCTCCAGTTC-3' | 270 | 301 |
| LDL-R | 5'-CAATGTCTCACCAAGCTCTG-3' | 5'-TCTGTCTCGAGGGGTAGCTG-3' | 258 | 301 |
| HMG | 5'-TACCATGTCAGGGGTACGTC-3' | 5'-CAAGCCTAGAGACATAATCATC-3' | 246 | 303 |
| IL-1α | 5'-GTCTCTGAATCAGAAATCCTTCTATC-3' | 5'-CATGTCAAATTTCACTGCTTCATCC-3' | 420 | 308 |
| IL-1β | 5'-AAACAGATGAAGTGCTCCTTCCAGG-3' | 5'-TGTTTCAGATCCCTTTAGTTCCAG-3' | 388 | 306 |
| IL-2 | 5'-GAATGGAATTAATAATTACAAGAATCCC-3' | 5'-TCCAGAACACCCACTTGTTGCTCCA-3' | 222 | 305 |
| PDGF-R | 5'-TGACCACCCAGCCATCCTTC-3' | 5'-GAGGAGGTGTTGACTTCATTC-3' | 228 | 300 |
| LPL | 5'-GAGATTTCTCTGTATGGCACC-3' | 5'-CTGCAAATGACACTTTCTC-3' | 277 | 300 |

TNF, tumor necrosis factor; M-CSF, macrophage-colony stimulating factor; PDGF-A, platelet-derived growth factor A; PDGF-B, platelet-derived growth factor B; apo-E, apolipoprotein E; LDL-R, low density lipoprotein receptor; HMG, 3-hydroxy-3-methylglutaryl coenzyme A reductase; IL-1α, interleukin-1α; IL-1β, interleukin-1β; IL-2, interleukin-2; PDGF-R, type β platelet-derived growth factor receptor; LPL, lipoprotein lipase.

Other mRNA targets which may be readily quantitated in biological samples by the present invention include, but are not limited to, granulocyte-colony stimulating factor (G-CSF), granulocyte macrophage-colony stimulating factor (GM-CSF), acidic-fibroblast growth factor (aFGF), basic-fibroblast growth factor (bFGF), c-McDonough feline sarcoma (c-fms), transforming growth factor-β (TGF-β), leukocyte adhesion protein-1 (LFA-1), interleukin-2 receptor-α (IL-2Rα), alpha-actin, desmin, β-actin, interleukin-6 (IL-6), interferon-α (IFN-α), interferon-γ (IFN-γ), interleukin-6 receptor (IL-6R), platelet derived growth factor-α receptor (PDGF-αR), interleukin-2 receptor-β (IL-2Rβ), interleukin-3 (IL-3), and interleukin-4 (IL-4) as well as human immunodeficiency virus (HIV). Examples of primer pairs useful for the detection and measurement of expression of these RNAs are exemplified by the oligonucleotide sequences shown in Table II.

TABLE II

| | |
|---|---|
| G-CSF | 5'GGTGAGTGAGTGTGCCACCT3', 5'GTTCTTCCATCTGCTGCCAG3'; |
| GM-CSF | 5'CACTGCTGCTGAGATGAATGAAACAG3', 5'GCACAGGAAGTTTCCGGGGTTGG3'; |
| aFGF | 5'TCCTTCCGGATGGCACAGTC3', 5'CATTTGGTGTCTGTGAGCCG3'; |
| bFGF | 5'GACCCTCACATCAAGCTACAAC3', 5'GGAAGAAAAGTATAGCTTTCTGC3'; |
| c-fms | 5'CAAGTATAAGCAGAAGCCCAAGTAC3', 5'GAGGGTCTTACCAAACTGCAGG3'; |
| TGF-β | 5'CATCAACGGGTTCACTACCG3', 5'TCCGTGGAGCTGAAGCAATAG3'; |
| LFA-1 | 5'GAGTGCCTGAAGTTCGAAAAGG3', 5'CACACACTCTCGGCTCTCATC3'; |
| IL-2Rα | 5'GCTGCCAGGCAGAGCTCTGTGACG3', 5'GTTCCGAGTGGCAGAGCTTGTGC3'; |
| α-actin | 5'GCACAACTGGCATCGTGCTG3', 5'AGACTCCATCCCGATGAAGG3'; |
| desmin | 5'AGGAGAGCCGGATCAACCTTC3', 5'TCGCTGACGACCTCTCCATC3'; |
| β-actin | 5'CCTTCCTGGGCATGGAGTCCTG3', 5'GGAGCAATGATCTTGATCTTC3'; |
| IL-6 | 5'CCTTCTCCACAAGCGCCTTC3', 5'GGCAAGTCTCCTCATTGAATC3'; |
| IFN-α | 5'AGCTGCAAGTCAAGCTGCTC3', 5'TCCCAAGCAGCAGATGAGTC3'; |
| IFN-γ | 5'GAAGAATTGGAAAGAGGAGAGTGACAGAAA3', 5'CATTCAAGTCAGTTACCGAATAATTAGTCAG3'; |
| IL-6R | 5'CATTGCCATTGTTCTGAGGTTC3', 5'AGTAGTCTGTATTGCTGATGTC3'; |
| PDGF-αR | 5'CTGGATGAGCAGAGACTGAG3', 5'AGGAAGCTGTCTTCCACCAG3'; |
| IL-2Rβ | 5'TTTCAGGTGCGGGTCAAGCCTCTG3', 5'AGTAACCCTGGTTGGTGAAGCAGC3'; |
| IL-3 | 5'CATGAGCCGCCTGCCCGTCC3', 5'GGTTATTTTCCATCAGAATG3'; |
| IL-4 | 5'CTCACCTCCCAACTGCTTCCC3', 5'GTGGAACTGCTGTGCAGTCGC3'; and |
| HIV | 5'AGTGGGGGGACATC3', 5'TTTGGTCCTTGTCTTATG3'. |

The PCR product from each primer set within pAW108 and pAW109 is 300–308 base pairs (bp), depending on the particular primer pair used. The 300–308 bp segment length of the illustrated example does not impose a limitation to the design of any internal standard. It is only necessary that the standard segment length is designed to be different in size from the PCR products of the target mRNAs and that the segment lengths be within the detection limits inherent in the analytical system preferred (for example, acrylamide gel electrophoresis, agarose gel electrophoreses, or other chromatographic means). The size difference between the PCR amplification products permits easy separation of the internal standard cRNA amplification product from the target mRNA amplification product by, for example, gel electrophoresis. The unique BamHI site is used to linearize the AW108 or AW109 plasmid to produce cRNA transcripts. Such transcripts are useful for quantitation of a number of different specific mRNAs in, for example, treated and untreated samples. This method can be used to provide a transcriptional phenotype of a treated or untreated cell or tissue and thus provides for numerous clinical and research applications.

The cRNA and the target mRNA are reverse transcribed in the same reaction. In this way, the cRNA serves not only as a standard for mRNA quantitation, but also provides an internal mRNA control for the reverse transcription reaction. Reverse transcriptase requires a primer to initiate cDNA synthesis using an RNA template. In the practice of the present invention, this will be an oligonucleotide primer which hybridizes to both the standard cRNA and the target mRNA. The primer may be identical in sequence to the 3' primer used for PCR amplification of that target mRNA. Alternatively, the primer for the reverse transcription reaction may be an oligonucleotide which hybridizes to the mRNA and cRNA at a position distal to the sequence of the 3' amplification primer, for example, oligo (dT). Thus, the resultant cDNA contains within it a sequence identical to the sequence of the 3' amplification primer. In the preferred embodiment disclosed herein, AW108 cRNA, as well as AW109 cRNA, contain a polyadenylation sequence at the 3' end, and oligo (dT) is used as a primer for reverse transcription of the cRNA and mRNA templates. Additionally, oligo (dT) permits amplification of more than one target sequence from the same reverse transcriptase reaction mix.

The same primers are used in the PCR amplification of both the standard and target templates; therefore, there are no primer efficiency differences between amplification of the standard and the target RNAs. When dilution series of mixtures of the target mRNA and internal standard cRNA are amplified in the same tube, and the reaction is terminated in the exponential phase of the amplification, the amount of target mRNA that was present in the sample prior to amplification can be determined by extrapolating against the internal standard cRNA standard curve. The amount of DNA produced is plotted against the amount of starting material for both the standard and the target. The standard curve allows extrapolation of the target data to determine the amount of target in the starting material. This value may be expressed as molecules of target mRNA/ng total RNA. Alternatively, it may be determined as of percentage or an amount by weight, or as a copy number.

Alternatively, a method is provided for determining the amount of target mRNA by varying the number of amplification cycles. The amount of amplified products produced is plotted against the number of amplification cycles for both the standard and target segments. The plotted data illustrates that portion of the reactions wherein the rate of amplification is exponential. Therefore, a ratio of products formed can be equated to a ratio of starting materials to determine the initial amount of target segment present. This is done according to the formula:

$$\frac{N_{o(mRNA)}}{N_{o(cRNA)}} = \frac{N_{(mRNA)}}{N_{(cRNA)}}$$

where $N_o$ is the initial amount of material, and N is the amount of amplified product produced.

In another embodiment of the present invention, a third primer array is inserted into the internal standard plasmid between the 5' primer array and the 3' primer array. The third oligonucleotide array is comprised of a series of synthetic sequences wherein there is one sequence corresponding to each RNA for which the plasmid contains a 5' and 3' primer pair. This array is designed such that for each target RNA to be quantitated, the amplified product will contain within it a sequence identical to a portion of the third oligonucleotide array. Thus, both the amplified target and amplified standard DNA segments contain an identical internal segment providing a probe hybridization site, whereby for each primer pair, an oligonucleotide probe is useful to detect the amplified target as well as the amplified standard DNA.

Where a third oligonucleotide array is included in the standard plasmid, the PCR reaction can be carried out without the use of label. It is preferred that the reverse transcription and amplification reactions are carried out in separate tubes for each of the standard and target templates, rather than as a co-amplification. Following amplification, amount of product is quantiated by use of a dot blot format employing a single-stranded oligonucleotide probe which has a sequence corresponding to the internal sequence provided by the third primer array.

As an illustrative example of the present invention, the AW108 internal standard was used to determine the amount of several lymphokine mRNAs, including IL-1α mRNA, isolated from lipoplysaccharide (LPS)-induced and control cultures of human macrophages. Lymphokine mRNA levels were also measured in human atherosclerotic plaque tissue.

As provided by the present invention, target mRNA is quantified most accurately by using an internal standard having, in part, the same sequence as the target itself. Quantification of mRNA sequences by PCR amplification using an unrelated template as an internal standard provides only comparative data because of differences in efficiency between the primer pairs for the standard and the target mRNAs. This is inherent in the amplification process because PCR amplification is an exponential process. The extent of amplification (N) is given by the equation: $N = N_o(1 + eff)^n$ where $N_o$ is the initial amount of material, eff is the efficiency, and n is the cycle number. Thus, small differences in efficiency lead to large differences in the yield of PCR product and result in a misrepresentation of the amount of template present in a biological sample. Further, differences in primer efficiency are difficult parameters to regulate for quantitative analyses. The present invention overcomes these problems.

The significant contribution of primer efficiency in the accurate quantitation of a nucleic acid segment is underscored in an example below. AW108 cRNA was used as the template for PCR amplification of several different primer sets. The efficiency of amplification by these different primer sets, under the same PCR conditions, varies over a range of several orders of magnitude. This invention addresses itself to this issue, which is clearly critical in any attempt to quantitate mRNA expression by PCR, and overcomes the problem of primer efficiency by using the same primers for amplification of the target mRNA and the internal standard cRNA.

The present invention requires that the amplification of the standard and target segments of nucleic acid be carried out in the same reaction. In the preferred embodiment of the present invention, the reverse transcriptase reaction of the standard cRNA and target mRNA is also carried out in the same reaction. Those skilled in the art will recognize from the foregoing that one could quantitate a target nucleic acid by performing the standard and target reverse transcriptase and amplification reactions separately. However, the accuracy of such a method is dependent on the degree to which the reverse transcription and amplification steps proceed with similar efficiency for both amplifications. By performing both reverse transcriptase reactions in the same tube and both amplification reactions in the same reaction tube, one ensures excellent accuracy.

The amount of an amplified DNA fragment in a given sample can influence amplification efficiency. When a high template concentration is used, or occurs as a result of the PCR amplification, phenomena can occur which are limiting factors for efficient amplification. Such phenomena include substrate saturation of enzyme, product inhibition of enzyme, incomplete product strand separation, and product strand reannealing. These problems are readily avoided, however, by an initial titration of the specific target mRNAs to find the range of concentrations that gives exponential amplification over a defined range of cycle numbers. Accordingly, to obtain reliable quantitative evaluation of specific mRNA using the described invention, the range of concentrations for both the standard and target templates, as well as the number of amplification cycles, should be such that the reactions remain within the exponential phase.

Thus, in the preferred embodiment, the reaction conditions described make use of 50 ng–1 μg of total cellular RNA combined with approximately $2 \times 10^2$–$2 \times 10^7$ molecules of cRNA. As little as 50 pg cellular RNA is also suitable for purposes of the present invention. In the example described, as few as $1 \times 10^4$ molecules of IL-1α are detected. It is not necessary that mRNA be purified from a total RNA preparation in order to employ the method of the invention.

Samples suitable for analysis by this method may be of human or non-human origin; they may be derived from cultured samples, or isolated from dissected tissue or from cells of immunologically defined phenotype. The latter can be obtained by monoclonal antibody staining and fluorescence-activated cell sorter (FACS) isolation of enzyme-dissociated cells or by removal of specific areas from immunohistochemically stained slides. This will permit definitive identification of the cell types producing specific mRNAs.

The amount of amplified DNA generated in the method of the present invention can be measured in different ways. For instance, labeled primers wherein one or both members of any primer pair is labeled, or labeled nucleotides, can be used in PCR, and the incorporation of the label can be measured to determine the amount of amplified DNA. The label can be isotopic or non-isotopic. Alternatively the amount of amplified product can be determined by electrophoresis and visualization of the amplified product by staining or by hybridization with a labeled probe. Densitometry can be used to calculate the amount of product on a stained gel, or by extrapolation from an autoradiograph when labeled probe is used. When a labeled probe is used, the probe should be present in excess of the amplified product. In one such embodiment of the invention, primers are isotopically labeled and the resultant amplified products are electrophoresed on an acrylamide gel. The region where the product is expected to migrate is excised, and the amount of label present is determined by Cerenkov counting. The amount of label present is plotted versus the amount of known starting material.

The method of the invention requires that the amplified amounts of a template and standard segment produced in a single polymerase chain reaction be determined. Thus, the method requires that the amplified template segment be distinguishable from the amplified standard segment. If the segments are of different sizes, then it is relatively simple to distinguish one amplified segment from the other, i.e., the amplified products can be readily separated by gel electrophoresis. The present invention does not require that the amplified product be of different sizes, however, for other methods can be utilized to distinguish one amplified segment from another. For instance, the internal probe specific for one segment can be labeled differently than the internal probe specific for the other segment.

The quantitative method described herein is useful for analyses of in vivo biological samples. As is illustrated in the following example, quantitative PCR analysis of PDGF-A and B chain mRNA a human atherosclerotic lesion versus a normal blood vessel emphasizes the sensitivity of this approach in investigating the biology of cells and tissues in vivo. For example, when the present method was used to measure IL-1α and IL-1β mRNAs in atherosclerotic tissue, the results suggested that there may be inflammatory or immunological components in the pathogenesis of the disease.

Due to its high sensitivity, speed, and accuracy, the present quantitative PCR method can be used to study gene expression in a more extensive way than has been possible to date, allowing quantitative measurements of gene expression in a very small number of cells and from small amounts of tissue samples available from in vivo sources, such as biopsies. This technique can also provide information on changes in expression level of specific RNA molecules which may be valuable in the diagnosis and analysis of, for example, infectious disease states, cancer, metabolic disorders, and autoimmune diseases.

It will be apparent to those skilled in the art that the method of the present invention is amenable to commercialization as a kit for the quantitation of one or more nucleic acids in a sample. For example, in its simplest embodiment, such a kit would provide an internal standard and an appropriate oligonucleotide primer pair. In another embodiment, a kit may contain an internal standard, an appropriate oligonucleotide primer pairs, a DNA polymerase, a RNA polymerase, a reverse transcriptase, nucleotide triphosphates, restriction enzymes, buffers for carrying out cRNA and cDNA synthesis, restriction enzyme digests, and amplification by PCR. Further, the kits may contain a thermostable DNA polymerase; for example, the thermostable DNA polymerase Taq isolated from *Thermus aquaticus* as an agent of polymerization.

The method of the invention is exemplified below, but those skilled in the art will recognize the present invention is broadly applicable and in no way limited to the specific embodiments described below.

EXAMPLE 1

Methods

A. Preparation of Internal Standard and RNAs

A synthetic gene was constructed using a technique of oligonucleotide overlap extension and amplification by PCR. The procedure used was similar to that described by Ho et al. for use in site-directed mutagenesis (Ho et al., 1989, *Gene* 77: 51–59). After construction, the synthetic gene was subcloned into an Okayama-Berg vector containing the T7 polymerase promoter and a polyadenylated sequence. The resulting plasmid, AW108, is shown in FIG. 1. This plasmid was used as a template for transcription by T7 polymerase according to the transcription protocol of the manufacturer (Promega Biotec, Madison, Wis. The resulting AW108 cRNA product was purified by oligo(dT) chromatography and gel electrophoresis. Alternatively, pAW109 was used to prepare a cRNA standard. The cRNA product was purified by selective elution using the QIAGEN-tip spin column hybridization separator system (QIAGEN Inc., Studio City, Calif. followed by oligo(dT) chromatography. The Qiagen-tip was used according to manufacturer's instructions for purification of RNA and run off RNA transcripts.

For either AW108 cRNA or AW109 cRNA, the purified cRNA was quantitated by determining absorbance at 260 nm. The number of molecules present was determined based on the molecular weight of the transcript. AW108 cRNA is 1026 nucleotides in length, therefore, 1 mole = $3.386 \times 10^5$ gm ($1026 \times 330$). Thus, $3.386 \times 10^5$ gm contains $6 \times 10^{23}$ cRNA molecules. The number of molecules in 1 pg of AW108 cRNA is $(6 \times 10^{23})/(3.386 \times 10^5 \text{ gm}) = 1.77 \times 10^6$.

Total cellular RNA was isolated from macrophages and tissues by the method of acid guanidium thiocyanate-phenol-chloroform extraction according to Chomczynski et al., 1987, *Analyt. Biochem.* 162:156–159.

B. Purification of cRNA by Gel Electrophoresis

The cRNA prepared from pAW108 was electrophoresed in 1% low melt agarose, ultra pure grade, in TBE buffer. The region of the gel corresponding to 1 kb was cut out of the gel and melted in 0.2–0.4 ml of 0.1M NETS buffer (0.1M NaCl, 0.01M EDTA; 0.01M Tris-HCl, pH 7.4; 0.2% SDS) containing 1 mM 2-ME, in a water bath at 95° C. for 3–5 minutes and solidified quickly in an ice bucket. The samples were then frozen at −70° C. for at least two hours.

The frozen samples of melted agarose were thawed at 37° C. and centrifuged at top speed in an eppendorf centrifuge kept in the cold room. The agarose was pelleted out. The supernatant liquid was transferred to another eppendorf tube and extracted with a mixture of 100 μl phenol chloroform containing 1% isoamhl alcohol. The phenol was saturated with 0.1M NETS buffer. The aqueous phase was collected, and the RNA was ethanol precipitated. The RNA pellet was washed with 0.1 ml of 2M LiCl and then with 0.1 ml ethanol. The RNA was dried and then dissolved in an appropriate amount of sterile distilled water (2–100 μl) and was ready for reverse transcription.

C. Oligonucleotides Used for Amplification

Oligonucleotides were synthesized on a Biosearch (San Rafael, CA) DNA synthesizer. Most of the primers are RNA-specific primers. The 5′ primers spanned the junction of the first two exons and the 3′ primers spanned the junction of the next two exons. Alternatively, the 5′ primers spanned the junction of the first and second exons and the 3′ primers spanned the junction of the second and third exons. These sequences, the genes to which they correspond, and the sizes of amplified products obtained using the primers are shown in Table I.

D. cDNA Preparation

RNA was reverse transcribed into cDNA as previously described (see Gerard, 1987, *Focus* (Bethesda Research Labs) 9:5). A 10 μl reverse transcription reaction, containing 1 μg of total cellular RNA, $1.77 \times 10^2 - 1.77 \times 10^6$ molecules of AW108 cRNA, 1×PCR buffer (20 mM Tris-HCl, pH 8.3, 50 mM KCl, 2 mM MgCl$_2$, 100 μg/ml BSA), 1 mM DTT, 0.5 mM dNTP, 10 units RNasin (Promega Biotec), 0.1 μg oligo (dT)$_{12-18}$, and 100 units of BRL Moloney MuL V reverse transcriptase (Bethesda Research Laboratories) was prepared. The reaction was incubated at 37° C. for 60 minutes, heated to 95° C. for 5–10 minutes, then quickly chilled on ice.

E. Amplification Procedure

One tenth of the cDNA reaction mixture was diluted in a three-fold dilution series with 0.1 μg/μl tRNA, followed by adjustment to a final concentration of 1×PCR buffer, 50 μM dNTPs, 0.1 μM each of 5′ and 3′ primers, 1×10$^6$ cpm of $^{32}$P end-labeled primer and 1 unit of Taq DNA polymerase (Perkin-Elmer Cetus) in a total volume of 50 μl. The mixture was overlaid with 100 μl mineral oil to prevent evaporation and then amplified for 25 cycles with the Perkin-Elmer Cetus Thermal Cycler. Alternatively, one tenth of the cDNA reaction mixture was amplified using the same conditions as above with varying numbers of cycles. The amplification profile involved denaturation at 95° C. for 30 seconds, primer annealing at 55° C. for 30 seconds, and extension at 72° C. for 1 minute. Oligonucleotides were labeled with γ-$^{32}$P-ATP by using polynucleotide kinase and unincorporated nucleotides were removed on a Bio-Gel P-4 column.

F. Quantitative Analysis

Ten μl of each PCR reaction mixture were electrophoresed in 8% polyacrylamide gels in Tris/-borate/EDTA buffer. Gels were stained with ethidium bromide and photographed under UV-light irradiation. Appropriate bands were cut from the gel, and radioactivity was determined by Cerenkov counting. The amount of radioactivity recovered from the excised gel bands was plotted against the template concentrations. Data were plotted by exponential curve fitting with a Slide-Write Plus program (Advanced Graphics Software) The amount of target mRNA was quantitated by extrapolating against the AW108 cRNA internal standard curve.

G. Northern Blot Analysis

RNA was electrophoresed in a 1.5% agarose gel containing formaldehyde and transferred to a nitrocellulose filter in 20×SSC (1×SCC contained 0.15M sodium chloride and 0.015M sodium citrate). The blot was hybridized with $2 \times 10^6$ cpm of $^{32}$P end-labeled oligonucleotides per ml. Hybridization was for 4 hours at 55° C.

in 0.75M NaCl, 0.075M sodium citrate, pH 7.0, 20 mM sodium phosphate, pH 7.0, 5 mM EDTA, 200 µg yeast RNA per ml, and 1% sarkosyl (Sigma). The blot was washed in 1×SSC at 55° C. for 30 minutes and autoradiographed with intensifying screens at −70° C.

H. Macrophage Cultures

Human peripheral blood monocytes were isolated from buffy coat preparations by Ficoll/Hypaque gradient centrifugation followed by adherence to plastic for one hour. Adherent cells were then removed and replated at $10^6$ cells/well onto 6 well plates in RPMI 1640 medium supplemented with 2% fetal calf serum and 2000 units/ml recombinant macrophage-colony stimulating factor (Cetus Corporation). After ten days, half of the cultures were treated with 5 µg/ml LPS (Sigma). All the cultures were harvested for nucleic acid isolation 5 hours later.

I. Human Tissue Samples

The carotid endarterectomy sample was obtained during the course of a surgical operation with the informed consent of the patient. The RNA preparation of a histologically normal coronary artery was recovered from a heart transplant recipient.

EXAMPLE 2

Quantification of IL-1α in a Preparation of Human Macrophage Total RNA

As an example of the present method, the AW108 internal standard was used to determine the amount of IL-1α mRNA isolated from LPS-induced cultures of human macrophages. Two different protocols were used to conduct this analysis. In the first case, the amount of template and standard RNAs was varied by serial dilution to generate a standard curve. In the second case, the number of amplification cycles was varied and plotted against the amount of PCR product.

A. Quantification of mRNA By Varying The Amount Of Internal Standard

Figure 2A:
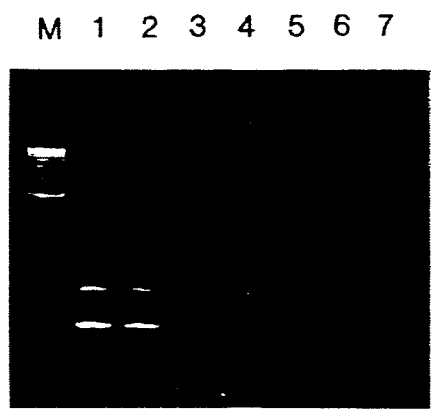
In FIG. 2A-C, the amount of IL-1α mRNA present in lipopolysaccharide (LPS) induced and uninduced macrophages was determined using the IL-1α primer pair.
Figure 2B:
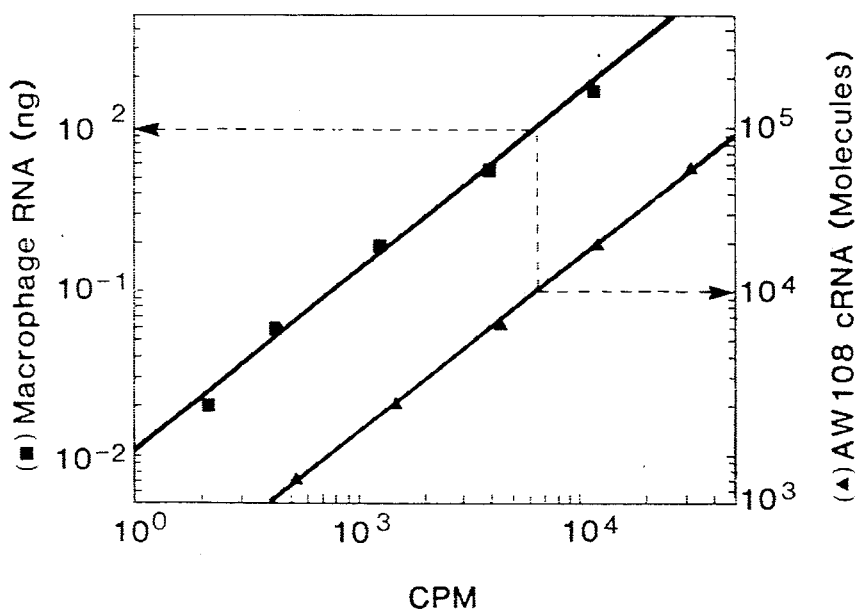

Fifty ng of total macrophage RNA and $1.77 \times 10^6$ molecules of AW108 cRNA were combined and then reverse transcribed into cDNA. Serial three-fold dilutions of one tenth of the cDNA mixture were amplified using the IL-1α specific primers listed in Table 1. About $1 \times 10^6$ cpm of $^{32}$P end-labeled 5' primer were included in the amplification. Reaction products were resolved by gel electrophoresis and visualized by ethidium bromide staining (FIG. 2A). The amounts of radioactivity recovered from the excised gel bands were plotted against the template concentrations (FIG. 2B). In this experiment, target mRNA and AW108 cRNA were amplified after serial three-fold dilutions, and the results demonstrate that the method can resolve less than three-fold differences in RNA concentrations. The fact that the reaction rates of AW108 cRNA and IL-1α mRNA amplification are identical within this exponential phase of the PCR reaction allows construction of a standard curve for AW108 cRNA and extrapolation to a copy number for the IL-1α mRNA present in the macrophages. As shown in FIG. 2B, 1 ng of LPS-induced macrophage total RNA and $1 \times 10^4$ molecules of AW108 cRNA gave the same amount of IL-1α PCR product. In other words, 1 ng of LPS-induced macrophage RNA contained $1 \times 10^4$ molecules of IL-1α mRNA.

B. Quantification of mRNA by Varying The Number of Amplification Cycles

Figure 2C:
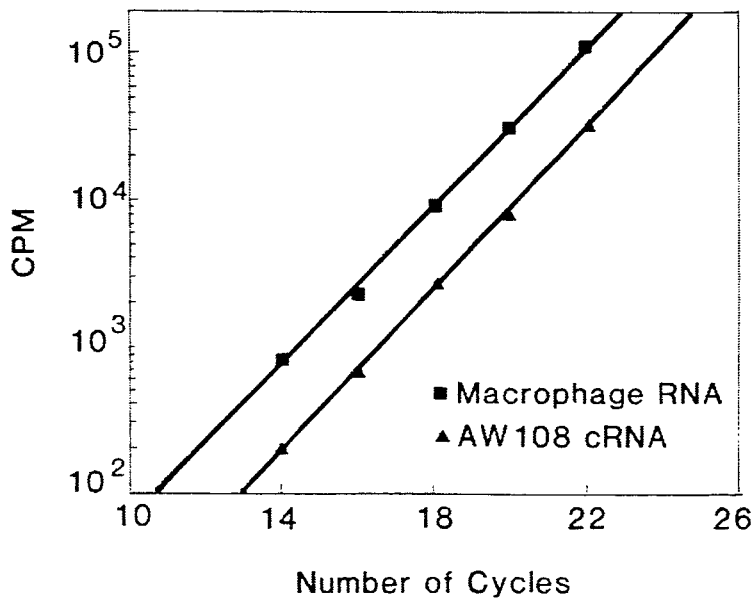

Five hundred ng of total macrophage RNA were reverse transcribed with $1.77 \times 10^6$ molecules of AW108 cRNA. Aliquots containing one tenth of the cDNA mixture each were subjected to 14, 16, 18, 20, 22, 24, 26, or 28 cycles of amplification under the same conditions as in protocol E. The amounts of radioactivity recovered from the excised bands were plotted as a function of the number of cycles (FIG. 2C). The rates of amplification were exponential between 14 and 22 cycles for both templates. At 24, 26, and 28 cycles, the rates decreased drastically and approached a plateau. The efficiency of amplification was calculated from the slopes of these curves and found to be 88% for both AW108 cRNA and IL-1α mRNA. Because the amplification efficiency was the same for both co-amplified targets within the exponential phase, the absolute value of IL-1α mRNA can be calculated by comparison with the AW108 cRNA internal standard employing the formula:

$$\frac{N_{o(mRNA)}}{N_{o(cRNA)}} = \frac{N_{(mRNA)}}{N_{(cRNA)}}$$

where $N_o$ is the initial amount of material, and N is the extent of amplification. The amount of IL-1α mRNA in 1 ng of LPS-induced macrophage total RNA calculated by this method was $1.1 \times 10^4$ molecules. Thus, the results using either of these two alternative protocols for quantitation are the same.

C. Correlation of PCR Results with Northern Analysis

Figure 3:
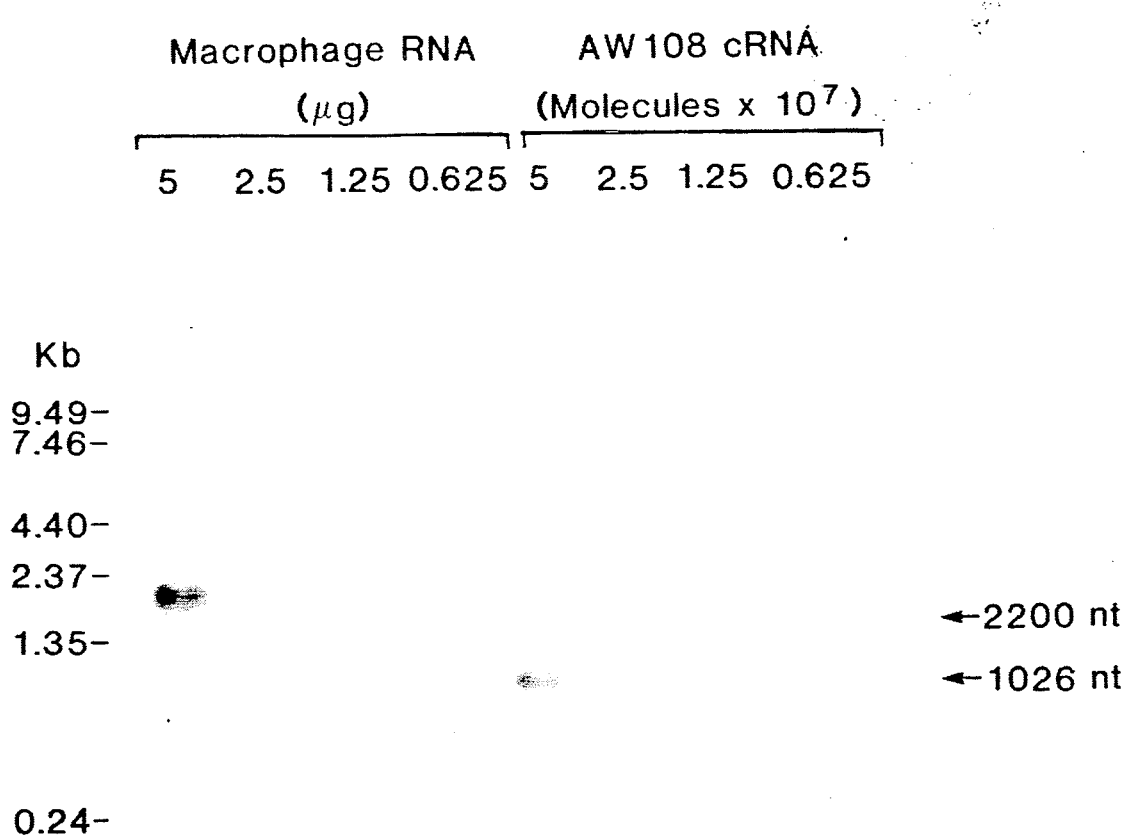
FIG. 3 shows the results of a Northern blot containing samples of AW108 cRNA, and RNA isolated from LPS induced macrophages. The blot was probed with the IL-1α 3' primer.
Figure 4:
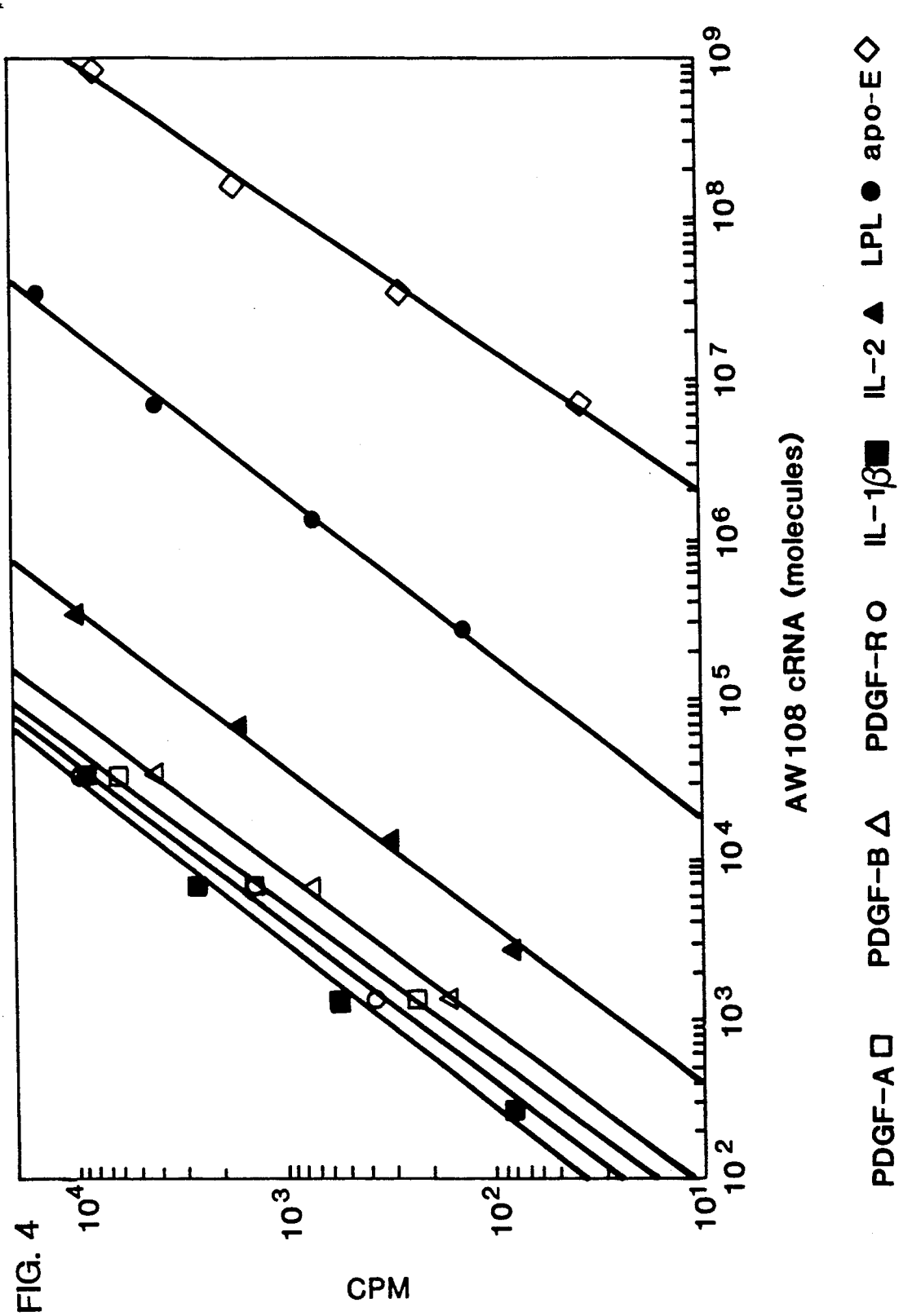
FIG. 4 shows the efficiency of amplification for different primer sets using the same cRNA template under the same conditions.

The amount of IL-1α mRNA in LPS-induced macrophages determined by the quantitative PCR method was verified by Northern blot analysis. The PCR analysis (see above) demonstrated that 1 ng of macrophage RNA and $1 \times 10^4$ molecules of AW108 cRNA produced the same amount IL-1α PCR product. Thus, 5 µg of macrophage RNA and $5 \times 10^7$ molecules of AW108 cRNA should give similar signal intensities by Northern analysis. Two-fold serial dilutions of macrophage RNA and AW108 cRNA were subjected to Northern blot analysis by probing with the IL-1α 3' primer. The sizes of the target RNA molecules were estimated to be ~2,200 nucleotides for IL-1α mRNA in macrophages and 1026 nucleotides for AW108 cRNA. Hybridization signals of equal intensity were detected at all the dilutions of macrophage RNA and AW108 cRNA, as shown in FIG. 3. This result demonstrates that the amount of mRNA estimated by the quantitative PCR method correlates with the results of Northern analysis.

EXAMPLE 3

Effect of Primer Efficiency Differences

There are many variables which could influence the effciency of the PCR amplification. Some of the parameters which can be controlled easily are the concentrations of template, dNTPs, MgCl$_2$, primers, polymerase, and PCR cycle profile. However, differences in primer efficiency are difficult parameters to regulate for quantitative analyses. To analyze the primer efficiency effect in the quantitative PCR method, AW108 cRNA was used as the template for PCR amplification of seven different primer sets: IL-1β, PDGF-B, PDGF-B, PDGF-R, IL-2, LPL, and apo-E. As indicated in FIG.

4, the efficiency of amplification by these different primer sets under the same PCR amplification conditions varied over a range of several orders of magnitude. For instance, the IL-1β primers are $10^5$-fold more efficient than the apo-E primers. Thus, it is critical to use the same primers for amplification of the target mRNA and the internal standard in any attempts to quantitate mRNA expression by PCR.

EXAMPLE 4

Quantitation of Specific mRNAs in Untreated and LPS-Induced Macrophages

A major advantage of the present PCR quantitative techniques is that the method enables one to analyze several target mRNA species in parallel. Table III shows the results from quantitation of the expression levels of six cytokine mRNAs in human macrophages in response to LPS treatment. The levels of IL-1β and IL-1α mRNAs, after LPS induction, increased approximately 50-fold. The levels of mRNAs for PDGF-A, M-CSF, and TNF increased 5 to 10-fold. However, the PDGF-B mRNA level remained constant for control and LPS-treated cells. Because the absolute amount of each mRNA was measured, this approach produces a detailed, yet multifaceted picture of the transcriptional phenotype in both the resting and the induced states using only fractions of micrograms of total RNA.

TABLE III

Specific mRNA levels (molecules/cell)* in LPS-Induced and Uninduced Human Macrophages**

| mRNA Species | Uninduced | Induced | Induced/Uninduced |
|---|---|---|---|
| IL-1α | 1.4 | 69 | 49 |
| IL-1β | 51 | 2,950 | 58 |
| PDGF-A | 0.05 | 0.48 | 10 |
| PDGF-B | 0.47 | 0.47 | 1 |
| M-CSF | 0.06 | 0.47 | 8 |
| TNF | 1.8 | 8.4 | 4.7 |

*Molecules/cell = molecules/μg RNA (calculated as in FIG. 2) × μg RNA isolated per cell.
**Monocyte-derived macrophages were cultured for ten days. 5 hours prior to harvest, half of the cultures were exposed to 5 μg/ml LPS.

EXAMPLE 5

Quantitative Analysis of Normal and Atherosclerotic Human Blood Vessels

Because accurate quantitative results can be obtained by the present technology even with small amounts of material, the method is an important tool for the analysis of samples which are rare or in limited quantity, e.g., in vivo-derived biopsy specimens. As an example, Table IV depicts the comparison of the results of quantitation of six different mRNA species from a human, atherosclerotic carotid artery and from a normal coronary artery. The data shows a 3- to 5-fold enhancement in the level of PDGF-A and PDGF-B mRNAs, no change in the type β PDGF receptor (PDGF-R) and a 3-fold decrease in the LDL receptor in the atherosclerotic vessel. There were increases in the levels of IL-1α and IL-1β mRNAs in the diseased tissue.

TABLE IV

Specific mRNA Levels (Molecules/μg Total RNA)* in a Normal and an Atherosclerotic Blood Vessel

| mRNA Species | Atherosclerotic | Normal |
|---|---|---|
| PDGF-A | $1.8 \times 10^5$ | $3.3 \times 10^4$ |
| PDGF-B | $7.6 \times 10^4$ | $2.2 \times 10^4$ |
| PDGF-R | $1.1 \times 10^4$ | $1.4 \times 10^4$ |
| LDL-R | $4.0 \times 10^3$ | $1.3 \times 10^4$ |
| IL-1α | $1.0 \times 10^2$ | ND** |
| IL-1β | $6.4 \times 10^4$ | $1.0 \times 10^2$ |

*Calculated as in FIG. 2.
**ND, Not Detectable

Other modifications of the embodiments of the invention described above that are obvious to those of ordinary skill in the areas of molecular biology, medical diagnostic technology, biochemistry, virology, genetics, and related disciplines are intended to be within the scope of the accompanying claims.

We claim:

1. A method for quantifying a target nucleic acid segment in a sample, which method comprises the steps of:
   (a) adding to said sample a predetermined initial amount of standard nucleic acid segment wherein said standard nucleic acid segment binds to same primers as are bound by said target nucleic acid segment in a reaction mixture;
   (b) treating said sample under conditions suitable for carrying out a polymerase chain reaction, wherein said nucleic acids are rendered single-stranded and exposed to an agent for polymerization, deoxynucleoside 5' triphosphates, and a pair of oligonucleotide primers, wherein said pair of primers is specific for both the target and standard nucleic acid segments, such that an extension product of each primer of said pair can be synthesized using separate strands of the target and standard segments as a template for synthesis, such that the extension product of one primer, when it is separated from the template strand, can serve as a template for the synthesis of the extension product of the other primer of said pair wherein said amplified target and standard segments are distinguishable by size or by the use of internal probes, wherein said internal probes may be differentially labeled for each of said amplified target and standard segments;
   (c) separating the primer extension product from the templates on which they were synthesized to form single-stranded molecules;
   (d) repeating steps (b) and (c) on the single stranded molecules produced in step (c) at least once, whereby each repeat of steps (b) and (c) is one amplification cycle;
   (e) measuring the amounts of the amplified target and standard segments produced in step (d); and
   (f) calculating from the amplified target and standard segments produced in step (d) the amount of said target nucleic acid segment present in the sample before amplification.

2. The method of claim 1 further comprising the step of preparing at least one dilution from the mixture of step (a) prior to step (b), whereby the amount of standard and target nucleic acid segments prior to said amplification reaction are varied.

3. The method of claim 1 wherein from 10 to 50 amplification cycles are performed, and wherein samples of said reaction mixture are removed and used to determine through which cycles the reaction is in exponential phase.

4. The method of claim 1 wherein said target nucleic acid segment is an mRNA molecule; said standard nucleic acid is a cRNA molecule; and said RNAs are reverse transcribed into cDNA molecules following step (a) and prior to step (b).

5. The method of claim 4 wherein the nucleic acid sequence of said cRNA molecule is synthesized using a plasmid template selected from the group AW108 and AW109.

6. The method of claim 4 wherein the pair of oligonucleotide primers of step (b) is labeled, and the amounts of amplified target and standard segments produced are measured according to step (e) by determining the amount of label incorporated into each of said amplified nucleic acid segments.

7. The method of claim 6 wherein said target nucleic acid segment is contained within an mRNA sequence, wherein said mRNA sequence encodes a lymphokine.

8. The method of claim 6 wherein said target nucleic acid segment is contained within a nucleic acid sequence, wherein said nucleic acid sequence encodes a protein selected from the group consisting of TNF, M-CSF, PDGF-A, PDGF-B, PDGF-R, apo-E, LDL-R, HMG, IL-1, IL-2, LPL, G-CSF, GM-CSF, aFGF, bFGF, c-fms, TGF-β, LFA-1, IL-2Rα, α-actin, desmin, β-actin, IL-6, IFN-α, IFN-γ, IL-6R, PDGF-αR, IL-2Rβ, IL-3, IL-4, and HIV proteins.

9. The method of claim 8 wherein said sample is a human blood cell sample or a human arterial vessel sample.

10. The method of claim 8 wherein said pair of oligonucleotide primers are selected from the group consisting of:

5'-CAGAGGGAAGAGTTCCCCAG-3',
5'-CCTTGGTCTGGTAGGAGACG-3';
5'-GAACAGTTGAAAGATCCAGTG-3',
5'-TCGGACGCAGGCCTTGTCATG-3';
5'-CCTGCCCATTCGGAGGAAGAG-3',
5'-TTGGCCACCTTGACGCTGCG-3';
5'-GAAGGAGCCTGGGTTCCCTG-3',
5'-TTTCTCACCTGGACAGGTCG-3';
5'-TTCCTGGCAGGATGCCAGGC-3',
5'-GGTCAGTTGTTCCTCCAGTTC-3';
5'-CAATGTCTCACCAAGCTCTG-3',
5'-TCTGTCTCGAGGGGTAGCTG-3';
5'-TACCATGTCAGGGGTACGTC-3',
5'-CAAGCCTAGAGACATAATCATC-3';
5'-GTCTCTGAATCAGAAATCCTTCTATC-3',
5'-CATGTCAAATTTCACTGCTTCATCC-3';
5'-AAACAGATGAAGTGCTCCTTCCAGG-3',
5'-TGGAGAACACCACTTGTTGCTCCA-3';
5'-GAATGGAATTAATAATTACAAGAATCCC-3',
5'-TGTTTCAGATCCCTTTAGTTCCAG-3';
5'-TGACCACCCAGCCATCCTTC-3',
5'-GAGGAGGTGTTGACTTCATTC-3'; and
5'-GAGATTTCTCTGTATGGCACC-3',
5'-CTGCAAATGAGACACTTTCTC-3'.

* * * * *

UNITED STATES PATENT AND TRADEMARK OFFICE
CERTIFICATE OF CORRECTION

PATENT NO. : 5,219,727
DATED : June 15, 1993
INVENTOR(S) : Alice M. Wang, Michael V. Doyle, and David F. Mark It is certified that error appears in the above-indentified patent and that said Letters Patent is hereby corrected as shown below:

Columns 7 and 8, Table I, under the section entitled "5' Primers", line 1,
please delete         "5'-CAGAGGGAAGACTTCCCCAG-3'"
and insert therefor   --5'-CAGAGGGAAGAGTTCCCCAG-3'--.

Columns 7 and 8, Table I, under the section entitled "3' Primers", line 4,
please delete         "5'-TTTCTCACCTGGACAGGTGG-3'"
and insert therefor   --5'-TTTCTCACCTGGACAGGTCG-3'--.

Columns 7 and 8, Table I, under the section entitled "3' Primers", line 9,
please delete         "5'-TGTTTCAGATCCCTTTAGTTCCAG-3'"
and insert therefor   --5'-TGGAGAACACCACTTGTTGCTCCA-3'--.

Columns 7 and 8, Table I, under the section entitled "3' Primers", line 10,
please delete         "5'-TCCAGAACACCACTTGTTGCTCCA-3'"
and insert therefor   --5'-TGTTTCAGATCCCTTTAGTTCCAG-3'--.

UNITED STATES PATENT AND TRADEMARK OFFICE
CERTIFICATE OF CORRECTION

PATENT NO. : 5,219,727
DATED : June 15, 1993
INVENTOR(S) : Alice M. Wang, Michael V. Doyle, and David F Mark It is certified that error appears in the above-indentified patent and that said Letters Patent is hereby corrected as shown below:

Columns 7 and 8, Table I, under the section entitled "3' Primers", line 12,
please delete    "5'-CTGCAAATGACACTTTCTC-3'"
and insert therefor    --5'-CTGCAAATGAGACACTTTCTC-3'--.

Column 7, Table II, line 5, please delete    "5'TCCTTCCGGATGGCACAGTC3'"
and insert therefor    --5'TCCTTCCGGATGGCACAGTG3'--.

Signed and Sealed this

Sixth Day of September, 1994

Attest:

BRUCE LEHMAN

Attesting Officer        Commissioner of Patents and Trademarks